United States Patent
Sugihara et al.

(10) Patent No.: US 9,943,333 B2
(45) Date of Patent: Apr. 17, 2018

(54) SPERM ACTIVATING AGENT AND ACTIVATING METHOD USING SAME

(71) Applicant: National University Corporation Hamamatsu University School of Medicine, Shizuoka (JP)

(72) Inventors: Kazuhiro Sugihara, Shizuoka (JP); Michiko Fukuda, San Diego, CA (US)

(73) Assignees: NATIONAL UNIVERSITY CORPORATION, Shizuoka (JP); HAMAMATSU UNIVERSITY SCHOOL OF MEDICINE, Shizuoka (JP)

( * ) Notice: Subject to any disclaimer, the term of this patent is extended or adjusted under 35 U.S.C. 154(b) by 118 days.

(21) Appl. No.: 14/429,632

(22) PCT Filed: Sep. 19, 2013

(86) PCT No.: PCT/JP2013/005538
§ 371 (c)(1),
(2) Date: Apr. 8, 2015

(87) PCT Pub. No.: WO2014/045582
PCT Pub. Date: Mar. 27, 2014

(65) Prior Publication Data
US 2015/0245852 A1 Sep. 3, 2015

(30) Foreign Application Priority Data
Sep. 20, 2012 (JP) .................. 2012-206711

(51) Int. Cl.
*A61B 17/435* (2006.01)
*C12N 5/076* (2010.01)
*A61K 38/18* (2006.01)
*A61K 38/47* (2006.01)
*A61D 19/04* (2006.01)
*C07K 14/50* (2006.01)
*C12N 9/38* (2006.01)

(52) U.S. Cl.
CPC ............ *A61B 17/435* (2013.01); *A61D 19/04* (2013.01); *A61K 38/1825* (2013.01); *A61K 38/47* (2013.01); *C07K 14/50* (2013.01); *C12N 5/061* (2013.01); *C12N 9/2468* (2013.01); *C12N 2501/115* (2013.01); *C12N 2501/119* (2013.01); *C12N 2501/73* (2013.01); *C12Y 302/01102* (2013.01); *C12Y 302/01103* (2013.01)

(58) Field of Classification Search
CPC .................. A61B 17/435; C12N 5/061
See application file for complete search history.

(56) References Cited

U.S. PATENT DOCUMENTS

2008/0200369 A1* 8/2008 Fukuda .................. C07K 7/06
514/1.1

FOREIGN PATENT DOCUMENTS

| JP | 2005-213147 A | 8/2005 |
| JP | 2005-255676 A | 9/2005 |
| JP | 2010-006785 A | 1/2010 |
| WO | 03046129 A2 | 6/2003 |

OTHER PUBLICATIONS

Shur et al., Sperm surface galactosyltransferase activites during in vitro capacitation, The Journal of Cell Biology, vol. 95, 1982, p. 567-573.*
Mukai, C. et al., "Function of Glycolysis in Sperm Motility," Journal of Mammalian Ova Research, vol. 27, No. 4, pp. 176 to 182 (Oct. 1, 2010), with its English translation.
Yurewicz, E.C. et al., "Porcine zona pellucida ZP3a glycoprotein mediates binding of the biotin-labeled Mr 55,000 family (ZP3) to boar sperm membrane vesicles," Molecular Reproduction and Development, vol. 36, No. 3, pp. 382-389 (1993).
Sutton-Smith, M. et al., "Analysis of protein-linked glycosylation in a sperm-somatic cell adhesion system," Glycobiology, vol. 17, No. 6, pp. 553-567 (2007).
Cotton, L.M. et al., "Cellular Signaling by Fibroblast Growth Factors (FGFs) and Their Receptors (FGFRs) in Male Reproduction," Endocrine Reviews, vol. 29, No. 2, pp. 193-216 (2008).
Sugihara, K. et al., "Translational Research Aiming at the Activation of Sperm Motility and the Improvement of Fertility Rate/Embryonic Development Rate", Acta Obstetrica et Gynaecologia Japonica, vol. 64, No. 2, p. 670 (S-544), P2-24-7 (Feb. 1, 2012) with its English translation.
Sugihara, K. et al., "Attenuation of fibroblast growth factor signaling by poly-N-acetyllactosamine type glycans," FEBS Letters, vol. 587, No. 19, pp. 3195-3201 (Oct. 1, 2013).
International Search Report for corresponding international application PCT/JP2013/005538, dated Dec. 24, 2103, including English translation.
European Search Report for European application No. 13839250.1, dated May 22, 2015.
Cotton, et al. "FGRF-1 signaling is involved in spermiogenesis and sperm capacitation," Journal of Cell Science, vol. 119, No. 1, pp. 75-84 and correction page, 2006.

* cited by examiner

*Primary Examiner* — Taeyoon Kim
*Assistant Examiner* — Tiffany M Gough
(74) *Attorney, Agent, or Firm* — Pearne & Gordon LLP (57) ABSTRACT

The present invention relates to an agent for activating mammalian sperm and a method for activating sperm by use of the activating agent. More specifically, the present invention relates to a sperm activating agent containing endo-β-galactosidase and/or FGF, which accelerate motility of mammalian sperm, for use in in-vitro fertilization and artificial insemination by husband and a sperm activating method by adding endo-β-galactosidase and/or FGF.

8 Claims, 10 Drawing Sheets

SPERM ACTIVATING AGENT AND ACTIVATING METHOD USING SAME

TECHNICAL FIELD

The present invention relates to an agent for activating mammalian sperm and a method for activating sperm by using the activating agent. More specifically, the present invention relates to a sperm activating agent containing endo-β-galactosidase and/or FGF, which accelerate motility of mammalian sperm, for use in in-vitro fertilization and artificial insemination and a sperm activating method by adding endo-β-galactosidase and/or FGF.

BACKGROUND ART

After ejaculation, mammalian sperm is activated for motility acquisition and capacitation. The activation process is a reaction, which takes place before the acrosome reaction or before sperm encounters egg and is a reversible reaction depending upon a decapacitation factor (DF) contained in the seminal fluid.

Motility acquisition of sperm is a phenomenon required for enabling the acrosome reaction of sperm. Furthermore, motility acquisition and capacitation simultaneously occur and these two sperm activation phenomena both are essential for fertilization. Capacitation is defined as a series of biochemical reactions caused by removal of a decapacitation factor. To cause these two phenomena, calcium and glucose are conceivably required.

A ketone body induces an active motion state of sperm and plays an important role in maintaining sperm's motility (Patent Literature 1). Further, many reports have focused on effect of e.g., an antioxidant on activation of sperm (Patent Literature 2, etc.).

Since an excessive amount of reactive oxygen inhibits action of sperm, an antioxidant has been drawn attention as an agent for activating sperm. For example, at present, a reactive oxygen removing substance such as glutathione, SOD and taurine is added; EDTA is added for the purpose of suppressing reactive oxygen and removing metal ions; and an antioxidant such as coenzyme Q10 and a catechin is used.

However, mechanism of action and clinical effect of these sperm activating agents have not yet been elucidated and an effective method for improving fertility has not yet been available in clinical sites.

CITATION LIST

Patent Literature

Patent literature 1: Japanese Patent Laid-Open No. 2005-255676
Patent literature 2: Japanese Patent Laid-Open No. 2005-213147

SUMMARY OF INVENTION

Technical Problem

An object of the present invention is to provide a novel sperm activating agent and sperm activating method effective for improving fertility.

Solution to Problem

The present inventors conducted intensive studies on the structure and motility of human sperm with a view to attaining the above object. As a result, they found that a large amount of glycan (polysaccharide) covering human sperm tail prevents access of a substance to the surface of sperm tail; one such glycan is a polylactosamine sugar chain having a special structure containing a large number of sulfuric acid groups and fucose; such a sugar chain is synthesized by the epithelial cells of the epididymis and secreted to the seminal fluid; and motility of sperm is enhanced by treating the sperm with endo-β-galactosidase; such an action occurs in accordance with an increase in cAMP level and calcium inflow; and FGFR2 is present in sperm tail and motility of sperm is enhanced by adding FGF to the sperm. Based on these findings, in particular, the finding that motility of sperm is accelerated by adding either endo-β-galactosidase or FGF, or a combination of endo-β-galactosidase and FGF to the sperm, the present inventors accomplished the present invention.

More specifically, the present invention provides the following [1] to [4].

[1] A sperm activating agent comprising endo-β-galactosidase and/or FGF.

[2] The sperm activating agent according to [1], in which the FGF is bFGF.

[3] A sperm activating method, including a step of adding endo-β-galactosidase and/or FGF to isolated sperm.

[4] The sperm activating method according to [3], in which the FGF is bFGF.

Advantageous Effects of Invention

The present invention provides a sperm activating agent and a sperm activating method based on an entirely new mechanism of action. Since motility of sperm is enhanced by using the sperm activating agent of the present invention, fertilization is consequently accelerated. The activating agent and activating method of the present invention can be utilized in in-vitro fertilization-embryo transfer (IVF-ET) of mammals including humans. In addition, it is considered that the present invention can tremendously improve the efficiency of artificial insemination by husband (AIH) for patients with infertility caused by sperm immotility.

BRIEF DESCRIPTION OF DRAWINGS

FIG. 1 shows CASA results of sperm motility. The sperm cells obtained from 19 volunteers were treated with endo-β-galactosidase at 37° C. for 15 minutes before analysis are represented by (+) and the sperm cells not treated are represented by (−). Reference symbol A shows total motility; reference symbol B shows motility of processive movement; and reference symbol C shows motility of non-progressive movement. The paired two-tailed t-test (n=19) was used as statistical analysis.

DESCRIPTION OF EMBODIMENTS

1. Definition

Endo-β-galactosidase (EBG) is an enzyme of hydrolyzing a β-galactoside bond within a poly-N-acetyl-lactosamine sugar chain. The endo-β-galactosidase that can be used in the present invention is not particularly limited as long as it has endo-β-galactosidase activity.

The "endo-β-galactosidase activity" used herein refers to the activity of hydrolyzing a bond between Galβ1 and 4GlcNAc (or Glc) contained in Galβ1-4GlcNAc (or Glc) contained in R-GlcNAcβ1-3Galβ1-4GlcNAc (or Glc) (R—N-acetylglucosamineβ1-3 galactoseβ1-4N-acetylglucosamine) (or glucose) to produce R-GlcNAcβ1-3Gal and GlcNAc (or Glc). Examples of the endo-β-galactosidase that can be used in the present invention may include an endo-β-galactosidase produced in a genetic engineering technique, an endo-β-galactosidase commercially available and the amino acid sequence of an endo-β-galactosidase having a partial substitution, deletion or addition of amino acids but having an endo-β-galactosidase activity. More specifically, e.g., the endo-β-galactosidase obtained in accordance with Fukuda, M. N. (1981) J. Biol. Chem. 256, 3900-3905 can be used.

A fibroblast growth factor (FGF), which is a member of a family of growth factors involved in angiogenesis, wound healing and embryonic development, is known to play an important role in a growth and differentiation process of almost all cells and tissues derived from the mesoderm. FGFs are roughly divided into a group of basic fibroblast growth factors (bFGF) and a group of acidic fibroblast growth factors (aFGF) based on their isoelectric points. The bFGF is also known as FGF2, which binds to a fibroblast growth factor receptor (FGFR). In the present invention, the bFGF is preferably used. Examples of bFGF that can be used in the present invention may include a bFGF extracted from a mammalian organ, a bFGF produced in a genetic engineering technique, a commercially available bFGF and an amino acid sequence of a bFGF having a partial substitution, deletion or addition of amino acids but having a binding activity to FGFR.

In the specification, the "sperm activation" refers to acceleration of motility of sperm and the "sperm activating agent" is an agent for accelerating motility of sperm, thereby improving fertility.

Examples of the mammal to which the present invention can be applied may include, but not limited to, domestic animals such as a cow, a horse, a pig, a sheep and a goat, laboratory animals such as a mouse, a rat and a rabbit, pets such as a dog and a cat, and humans.

2. Agent for Activating Sperm

The present invention provides an agent for activating mammalian sperm comprising an endo-β-galactosidase and/or FGF. Accordingly, the sperm activating agent of the present invention can be used as a therapeutic agent for infertility caused by e.g., asthenospermia, a fertilization accelerator and an in-vitro fertilization accelerator.

The sperm activating agent of the present invention contains either endo-β-galactosidase or FGF, or a combination of endo-β-galactosidase and FGF as active ingredients. As the FGF, a bFGF is preferably used. The sperm activating agent of the present invention may further contain other components as long as they do not inhibit activation of mammalian sperm. Examples of the other components include pyruvic acid, glucose and hydroxybutyric acid serving as energy source for sperm motion.

The sperm activating agent of the present invention is used by adding it to sperm isolated from a mammal. Examples of the sperm may include sperm immediately after collected, sperm stored at normal temperature after collected and sperm cryopreserved and thawed. Also, the sperm activating agent of the present invention can be used as a component of a sperm culture medium and may be used by adding it to the sperm culture medium in advance or in culturing.

The sperm activating agent of the present invention contains an effective amount of endo-β-galactosidase and/or FGF for activating sperm. More specifically, the sperm activating agent of the present invention contains endo-β-galactosidase such that endo-β-galactosidase is used in a concentration of 0.1 to 5 mU/mL. The sperm activating agent of the present invention also contains FGF such that FGF is used in a concentration of 1 to 100 ng/mL. When the sperm activating agent of the present invention contains endo-β-galactosidase in combination with FGF, the contents of them may be each lower than that of single use.

3. Method for Activating Sperm

The present invention provides a method for activating mammalian sperm by adding endo-β-galactosidase and/or FGF to isolated sperm.

The sperm activating method of the present invention can be applied to sperm isolated from a mammal. Examples of the sperm may include sperm immediately after collected, sperm stored at normal temperature after collected and sperm cryopreserved and thawed. In an embodiment of the present invention, the sperm activating agent may be added to the seminal fluid and culture solution containing sperm.

The concentration of sperm can be appropriately set depending upon the type of subject mammal and the storage state of sperm. For example, when the method of the present invention is applied to human sperm, the concentration of sperm is set at $1\times10^5$ to $1\times10^7$ cells/mL.

In the sperm activating method of the present invention, either endo-β-galactosidase or FGF, or a combination of endo-β-galactosidase and FGF is added to sperm. When endo-β-galactosidase and FGF are added in combination, they are sequentially or simultaneously added. When they are added sequentially, a first component and a second component may be continuously added or a second component may be added at a predetermined time interval after a first component is added. When they are added sequentially, either one of them may first added; however, endo-β-galactosidase is preferably added first. Other components may be added as long as they do not inhibit activation of mammalian sperm. Examples of the other components include pyruvic acid, glucose and hydroxybutyric acid serving as an energy source for sperm motion.

In the sperm activating method of the present invention, effective amounts of endo-β-galactosidase and/or FGF for activating sperm are added. More specifically, endo-β-galactosidase is added such that endo-β-galactosidase is used in a concentration of 0.1 to 5 mU/mL and FGF is added such that FGF is used in a concentration of 1 to 100 ng/mL. In an embodiment of the present invention, when both endo-β-galactosidase and FGF are added, the contents of them may be each lower than that of single use.

In the sperm activating method of the present invention, the sperm may be cultured in a predetermined time (for example, 5 minutes, 15 minutes, 30 minutes, 60 minutes) after endo-β-galactosidase and/or FGF are added to sperm. The medium is not particularly limited, as long as it is suitable as a medium for culturing sperm. For example, in-vitro fertilization mediums known in the art such as BO liquid, KRB, KRP, TYH, TCM199 and SOF can be used. Note that the medium is preferably a "serum-free medium" containing no animal serum; however, e.g., a serum substitute and KSR (Knockout Serum Replacement) may be added. The pH of the medium preferably falls within the range of 5.5 to 9.0, preferably 6.0 to 8.0 and more preferably 6.5 to 7.5. The culturing is performed at room temperature to 38° C., preferably room temperature to 37.5° C., in the conditions of 1% to 25% of $O_2$ and 1% to 15% $CO_2$ while appropriately exchanging the medium.

The contents of all Patents and Literatures explicitly cited in the specification are incorporated herein in their entirety by reference. Furthermore, the contents described in the specification and drawings of Japanese Patent Application No. 2012-206711 (filed Sep. 20, 2012) based on which the priority of the present application is claimed are incorporated herein in their entirety by reference.

Now, the present invention will be more specifically described by way of Examples; however, these Examples will not be construed as limiting the present invention.

EXAMPLES

1. Experiment Method (1) Enzyme, Antibody and Expression Vector

Endo-β-galactosidase was obtained from SEIKAGAKU CORPORATION (Tokyo), and also purified from *E. freundii* culture medium, as described in Fukuda, M. N. (1981) J. Biol. Chem. 256, 3900-3905. A monoclonal anti-Lewis Y antibody (clone AH6, mouse IgM) was provided by Dr. S. Hakomori of University of Washington.

(2) CASA

Human sperm cells, which were obtained from 19 healthy volunteers and cryopreserved, were washed with a sperm washing medium (Irvine Biologicals) and suspended in the same type of solution. Endo-β-galactosidase was dissolved in water in a concentration of 1 mU/mL. Endo-β-galactosidase (5 mL) was added to 100 mL of a human sperm solution ($2\times10^6$ cells) and the mixture was incubated at room temperature for 15 minutes. Motility of the sperm cells was analyzed by use of a computer-aided seminal fluid analyzer (CASA, sperm quality analyzer-v, Medical Electronic systems, Los Angeles, Calif.). Statistical analysis was carried out by a student's t-test using Prism program (GraphPad Softwear).

(3) Measurement of ATP, Calcium Influx and cAMP

The level of ATP in human sperm cells was measured by ATP assay CellTiter-Glo (Promega) based on fluorescence. More specifically, human sperm cells were incubated in the presence of endo-β-galactosidase, as mentioned above and mixed with an equal amount of CellTiter-Glo reagent. Samples to be assayed in quadruplicate were placed in wells of a white 384-well plate and chemiluminescence was monitored every one minute up to 90 minutes by use of Beckman DTX810 plate reader. Calcium influx to sperm cells was measured by use of Fluo-4 NW calcium assay kit (Molecular Probes). Sperm cells treated with or without endo-β-galactosidase were assayed in triplicate in a 96 well plate. Fluorescence at an excitation wavelength of 485 nm and fluorescence at an excitation wavelength of 536 nm were measured every 30 seconds up to 180 minutes by use of FlexStation II plate reader (Molecular Devices). Cyclic AMP was measured by a competitive immunoassay kit for cAMP and GMP XP (Cell Signaling). More specifically, sperm cells were treated in the presence or absence of 2.5 U/mL of endo-β-galactosidase for 0, 15 or 60 minutes. Immunoassay was performed in triplicate in accordance with the manufacturer's protocol. The chemiluminescence value obtained from a control sample was subtracted from the value obtained from an endo-β-galactosidase treated sample.

(4) Preparation of Sperm Associated Glycan and Mass Spectrometry Thereof

Human sperm cells were obtained from 20 volunteers and cryopreserved. After thawing, the sperm cells were centrifugally collected, washed twice with a phosphate buffered saline (PBS) and digested with 20 μL of proteinase K (14 to 22 mg/mL, Roche) at 45° C. for 20 hours. After insoluble matter was centrifugally removed, the supernatant was treated with 0.5 M NaOH containing 1 M $NaBH_4$ at 37° C. for 20 hours. A sample was passed through Sephadex G-25 equilibrated with water. Substance dissolved in a void volume was pooled and applied to a Sephadex G-50 super fine column equilibrated with 0.2 M NaCl. Neutral sugars were monitored with the Anthrone color reaction and a glycopeptide having glycan having large molecular weight or a polylactosamine was collected for mass spectrometry. The sample was digested with 5 mM endo-β-galactosidase (derived from *E. freundii*, SEIKAGAKU CORPORATION) in 50 mM ammonium acetate at pH of 5.8 and 37° C. for 48 hours, and thereafter, allowed to flow from Supelclean ENVI-Carb cartridge (Supelco) with 25 to 50% acetonitrile in 0.1% TFA and completely methylated (permethylated). Other lots of the sample were directly and completely methylated for MALDI-MS and MS/MS under the aforementioned conditions in order to recover both non-sulfated glycan and sulfated glycan.

(5) Preparation of Spermatic Polylactosamine

Human seminal fluid was mixed with a 3-fold volume of a chloroform-methanol (2:1, v/v) mixture to extract lipids. After the mixture was centrifuged, the resultant pellet was suspended in a 0.1M Tris-HCl buffer containing 1 mM EDTA (pH 8.0) and digested with protease K at 45° C. for 20 hours. After the mixture was centrifuged, a water-soluble substance was passed through Sephadex G-25 equilibrated with water, the substance(s) extracted in a void volume was applied to a Sephadex G-50 super fine column, as mentioned above. A polylactosamine was collected, desalted by Sephadex G-25 column and lyophilized.

(6) Immunohistochemistry

Sections of paraffin-embedded tissues such as human testis, ductuli efferentes testis and ductuli epididymics were obtained from Folio Biosciences. After paraffin was removed from the tissue sections, the sections were subjected to hydration and treatment with peroxide. Thereafter, a pair of slides per tissue was subjected to an endo-β-galactosidase treatment performed at 37° C. for 30 minutes. The resultant tissue specimens were each stained with an anti-Lewis Y (clone AH6) antibody and subsequently with biotinylated goat anti-mouse IgM antibody (Vector) and peroxidase conjugated streptavidin. The peroxidase color reaction was performed by use of a DAB substrate or an AEC single solution (Invitrogen) and counter staining was performed with hematoxylin. Human sperm cells not washed and human sperm cells washed with PBS were smeared on slide glasses, dried in the air and fixed with 4% paraformaldehyde in PBS. Subsequently, the tissues were treated with or without endo-β-galactosidase and subjected to immuno-staining for tissue slices, as mentioned above.

(7) FGF Binding Assay

HEK293T cells were cultured up to a confluency of 75%. The medium was completely exchanged with a fresh medium containing 10% fatal bovine serum and 1 mM $Na_3VO_4$ every 30 minutes. The polylactosamine purified by the aforementioned method (1 mg/mL) was added to a monolayer and incubated for 10 minutes. Subsequently recombinant b-FGF (Sigma) was added to a final concentration of 25 ng/mL and incubation was performed for 5 minutes. Subsequently, the cells were washed three times with TBS. Cell lysates were prepared by use of a lysis buffer contained in b-FGF ELISA kit (Ray Biotech) and centrifuged. Each of the lysates containing 100 mg of protein was subjected to ELISA inhibition assay and the amount of FGF bound to the HEK293T cells was determined in the presence or absence of the polylactosamine.

(8) Immunoprecipitation and Immunoblot

HEK293T cells were cultured in a medium supplemented with 10% fatal bovine serum. $Na_3VO_4$ was added so as to obtain a final concentration of 1 mM and the cells were incubated for 30 minutes. FGF was added so as to obtain a final concentration of 25 ng/mL and the cells were incubated for 5 minutes in the presence or absence of a polylactosamine (1 mg/mL). Subsequently, the resultant cells were collected by rubber policeman, washed with cold TBS containing 1 mM $Na_3VO_4$ and lysed in 1% NP-40 in TBS. Each lysate was pre-cleaned by use of 20 μL protein A/G agarose beads at 4° C. for 20 hours. Protein A/G beads (20 μL) were coated with an anti-FGFR2 antibody (2 μg, rabbit polyclonal, GenTex) in TBST (500 μL) at 4° C. for 20 hours. The lysate pre-cleaned was reacted with anti-FGFR2 antibody-coated protein A/G beads at 4° C. for 20 hours. The beads were washed three times with TBST and the substance bound to the beads was extracted by boiling the beads in a SDS buffer for 3 minutes. The resultant protein was separated on a 4 to 12% density gradient SDS-polyacrylamide gel, transferred onto an immobilon-P filter (Millipore) and blocked with Odyssey blocking buffer (Li-Cor Biosciences). Thereafter, the filter was placed in a blocking buffer containing 0.1% Tween 20 and a diluted (1:500) anti-tyrosine phosphate antibody (4G10, Upstate Biologicals) and allowed to react for 60 minutes. Subsequently, incubation was performed together with a diluted (1:5000) IRDye-bound anti-mouse IgG antibody (Li-Cor Biosciences) for 45 minutes. After washed with TBST, the filter was scanned by Odyssey imaging system to detect a band.

(9) Acrobead Test

Human sperm cells were obtained from 5 volunteers and subjected to an acrobead test (MH61 antibody bound beads, Fuso Pharmaceutical Industries, Ltd.), in which a change of human sperm cells in fertility between the presence and absence of endo-β-galactosidase was evaluated. Fertility was determined and evaluated in accordance with the protocol attached to the acrobead test kit. To describe more specifically, fresh or lyophilized human sperm cells were washed with a sperm washing solution (Irvine Biologicals) and treated with or without endo-β-galactosidase (2.5 mU) at room temperature for 15 minutes. Sperm cells ($5 \times 10^6$ cells/mL) were serially diluted (1:1, 1:2, 1:4, and 1:8), added to flat-bottom microtiter plates containing acrobeads and incubated in a humidity incubator in the presence of $CO_2$ (5%) at 37° C. for 24 hours without stirring. Five regions in each well were observed under an inverted microscope. The result in which all sperm cells bound to the beads was determined as positive; whereas, the result in which none or only several of sperm cells bound to the beads was determined as negative. To the sample showing a positive result up to 1:8 dilution, score 4 was given; to the sample showing a positive result up to 1:4 dilution, score 3 was given; to the sample showing a positive results up to 1:2 dilution, score 2 was given; and the sample showing a positive results up to 1:1, score 1 was given (see Table 1). Statistical analysis was performed by paired two-tailed t-test using Prism program (GraphPad Softwear).

TABLE 1

| Criteria for scoring | | | | | |
|---|---|---|---|---|---|
| Dilution factor of sperm cells | | | Result | | |
| 1 | − | + | + | + | + |
| 2 | − | − | + | + | + |
| 4 | − | − | − | + | + |
| 8 | − | − | − | − | + |
| Score | 0 | 1 | 2 | 3 | 4 |
| Fertility of sperm cells | Not satisfactory | | Satisfactory | | Excellent |

+; Positive all sperm cells bind to beads)
−; Negative (none or only several of sperm cells bind to beads)

Figure 1:
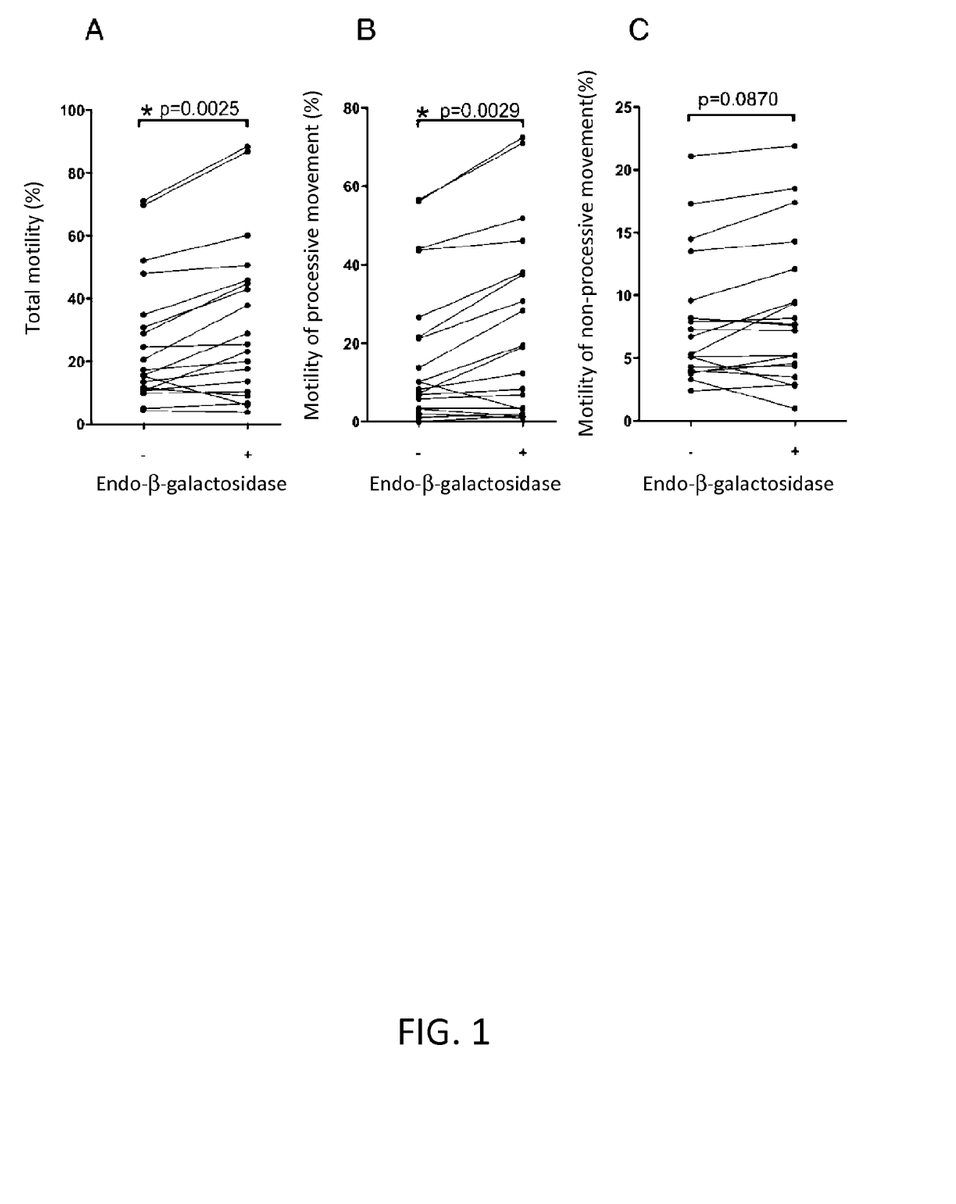

2. Results (1) Endo-β-Galactosidase Treatment Accelerates Mobility of Human Sperm Conventional studies including the research results of the present inventors suggest that matured human sperm cells are each densely covered with a sugar chain (Tollner, T. L., Venners, S. A., Hollox, E. J., Yudin, A. I., Liu, X., Tang, G., Xing, H., Kays, R. J., Lau, T., Overstreet, J. W., Xu, X., Bevins, C. L., and Cherr, G. N. (2011) Sci Transl Med 3, 92ra65, Hatakeyama, S., Sugihara, K., Lee, S. H., Nadano, D., Nakayama, J., Ohyama, C., and Fukuda, M. N. (2008) J Urol 180, 767-771, Pang, P. C., Tissot, B., Drobnis, E. Z., Sutovsky, P., Morris, H. R., Clark, G. F., and Dell, A. (2007) J Biol Chem 282, 36593-36602). To determine whether polysaccharides are involved in movement of sperm tail, the present inventors treated human sperm cells with endo-β-galactosidase (enzyme hydrolyzing poly-N-acetyl-lactosamine). Based on a visual examination, it was found that sperm cells treated with endo-β-galactosidase move more actively than the sperm cells not treated (data are not shown). To determine the type of movement accelerated by the endo-β-galactosidase treatment, sperm cells were subjected to computer-aided sperm analysis (CASA). From the analysis, it was found that motility of processive movement or motility of forward movement is accelerated by the enzyme treatment, motility of random or non-processive movement is not accelerated (FIG. 1).

Figure 10:
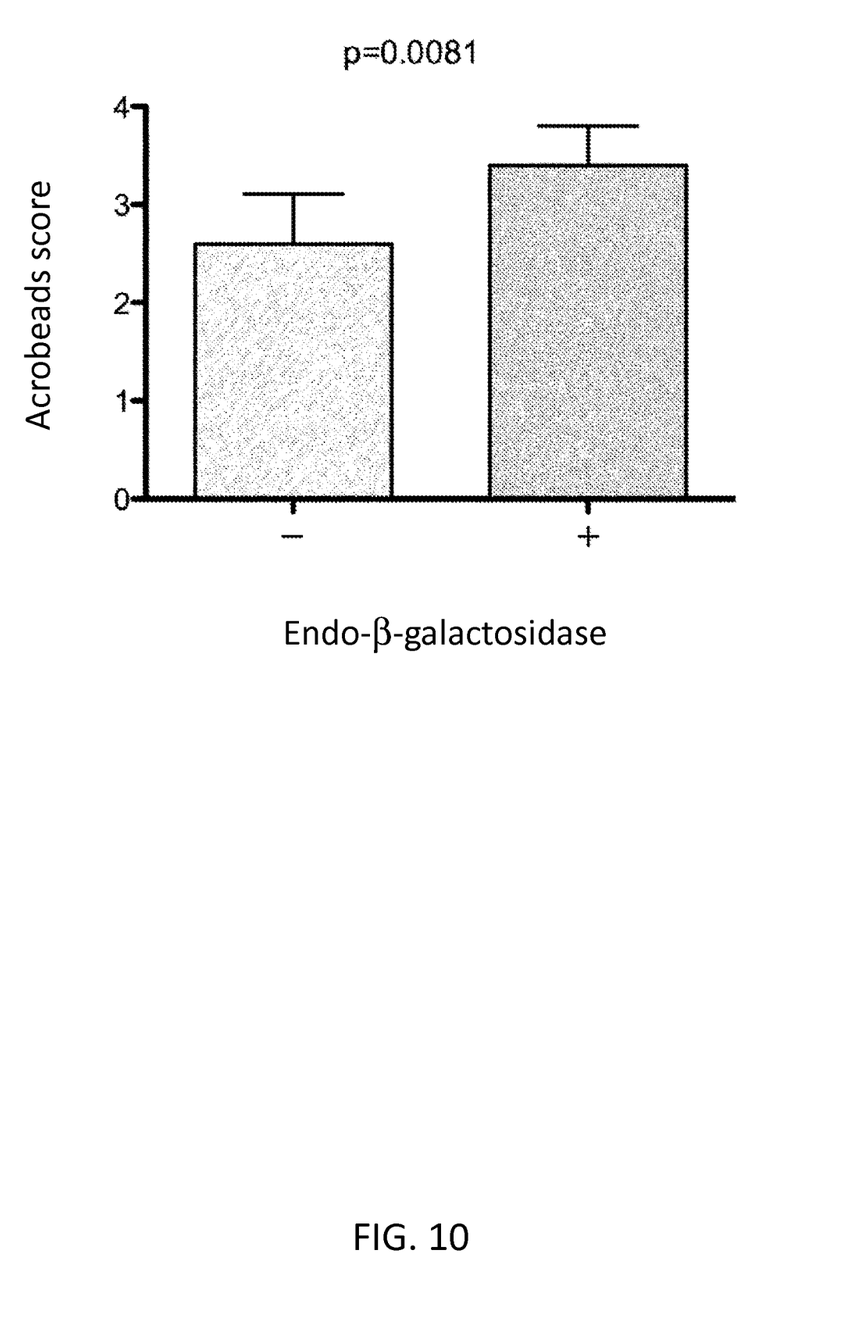
FIG. 10 shows the evaluation results of human sperm fertilizing ability using an acrobead test.

The present inventors evaluated a fertility change of human sperm cells treated with endo-β-galactosidase (EBG), by the acrobead test. The results suggested that fertility is accelerated by addition of EBG (FIG. 10).

Figure 2:
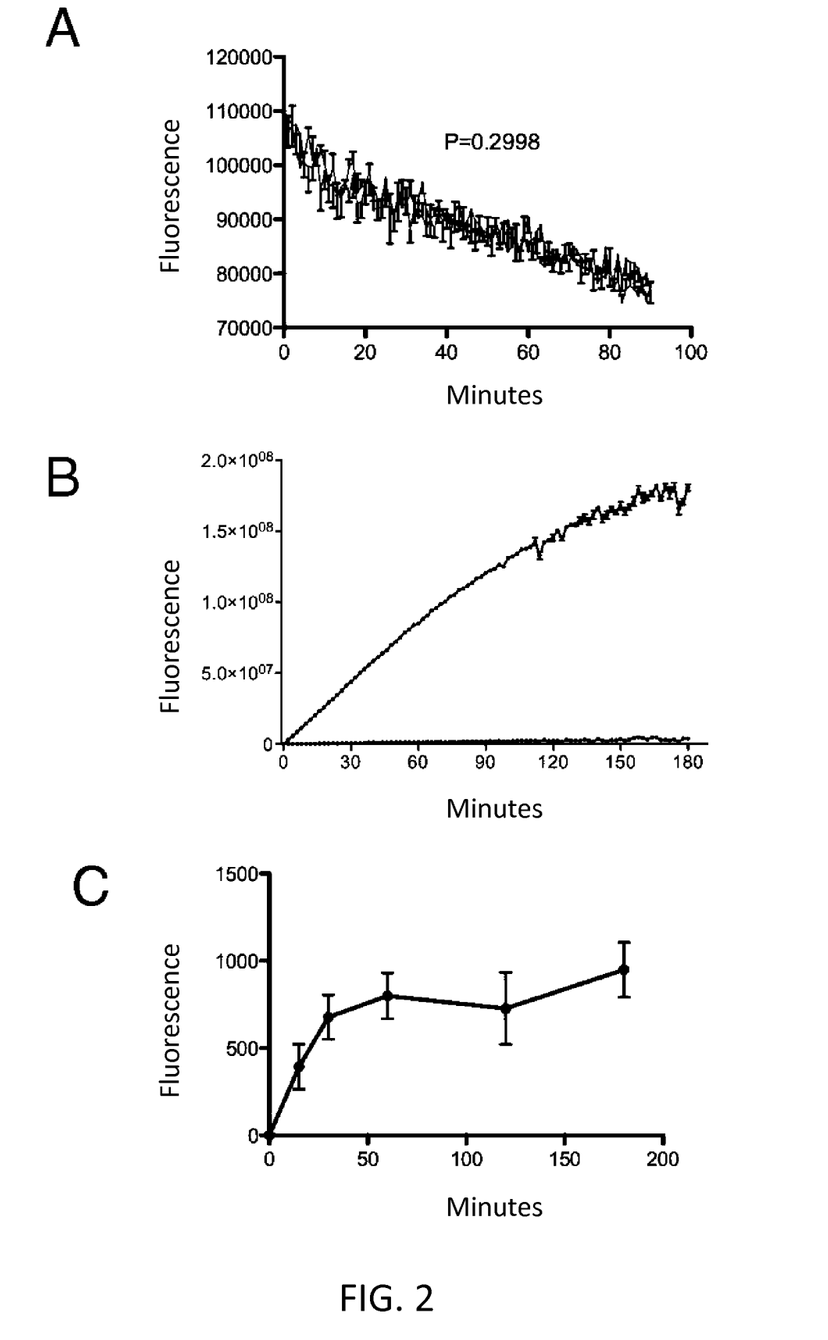
FIG. 2 shows graphs indicating the effects of endo-β-galactosidase treatment on human sperm. Reference symbol A shows the ATP level of human sperm treated with endo-β-galactosidase (indicated by red) and the ATP level of human sperm not treated (indicated by blue); reference symbol B shows the calcium level of human sperm treated with endo-β-galactosidase (indicated by red) and calcium level of human sperm not treated (indicated by blue); and reference symbol C shows the cAMP level of human sperm treated with endo-β-galactosidase and the cAMP level of human sperm not treated.

It has been reported that activation of ATPase and ion channel is required for motility of sperm tail. To analyze these parameters, the present inventors measured the ATP level in sperm cells; however, no difference was observed between a control group and a group treated with endo-β-galactosidase (FIG. 2A). In contrast, the calcium level in sperm cells treated with the enzyme significantly increased (FIG. 2B). Since calcium influx into sperm cells is regulated by cyclic nucleotide-dependent gated channels, the present inventors checked level of cAMP. As a result, they found that the cAMP level in the sperm cells treated with endo-β-galactosidase is certainly enhanced (FIG. 2C). These results strongly suggest that a polylactosamine bound to sperm tail regulates sperm motility via cAMP and calcium channel dependent mechanisms.

FIG. 2 shows graphs indicating the effects of treatment of endo-β-galactosidase on human sperm. Reference panel A shows the ATP level of human sperm cells treated with endo-β-galactosidase (indicated by red) and the ATP level of human sperm cells not treated (indicated by blue), each spot represents an average of the results of quadruplicate measurements; reference panel B shows the calcium level of human sperm cells treated with endo-β-galactosidase (indicated by red) and calcium level of human sperm cells not treated (indicated by blue), each spot represents an average of the results of triplicate measurements; and reference panel C shows the cAMP level of human sperm cells treated with endo-β-galactosidase and the cAMP level of human sperm cells not treated. Sperm cells were subjected to cAMP measurement based on protein kinase C. The value of fluorescence is obtained by subtracting the value of fluorescence derived from a control treated with a buffer during a test period from the value of fluorescence derived from the cells treated with endo-β-galactosidase. Each spot indicates an average of 10 readout data.

(2) Structure of Polylactosamine Isolated from Human Sperm Cells

To determine which type of sugar chain structure is involved in regulation of sperm motility, the present inventors isolated a polylactosamine from human sperm cells. Since a polylactosamine was not detected in previous studies on human sperm glycan, the present inventors predicted that a polylactosamine is not a component intrinsically present in human sperm but a component in connection with the tail. To characterize the polylactosamine in connection with sperm, the present inventors isolated sperm cells from the seminal fluid after washed twice with PBS. The sperm cells were thereafter digested with protease K and a water soluble substance was fractionated by gel filtration chromatography.

Figure 3:
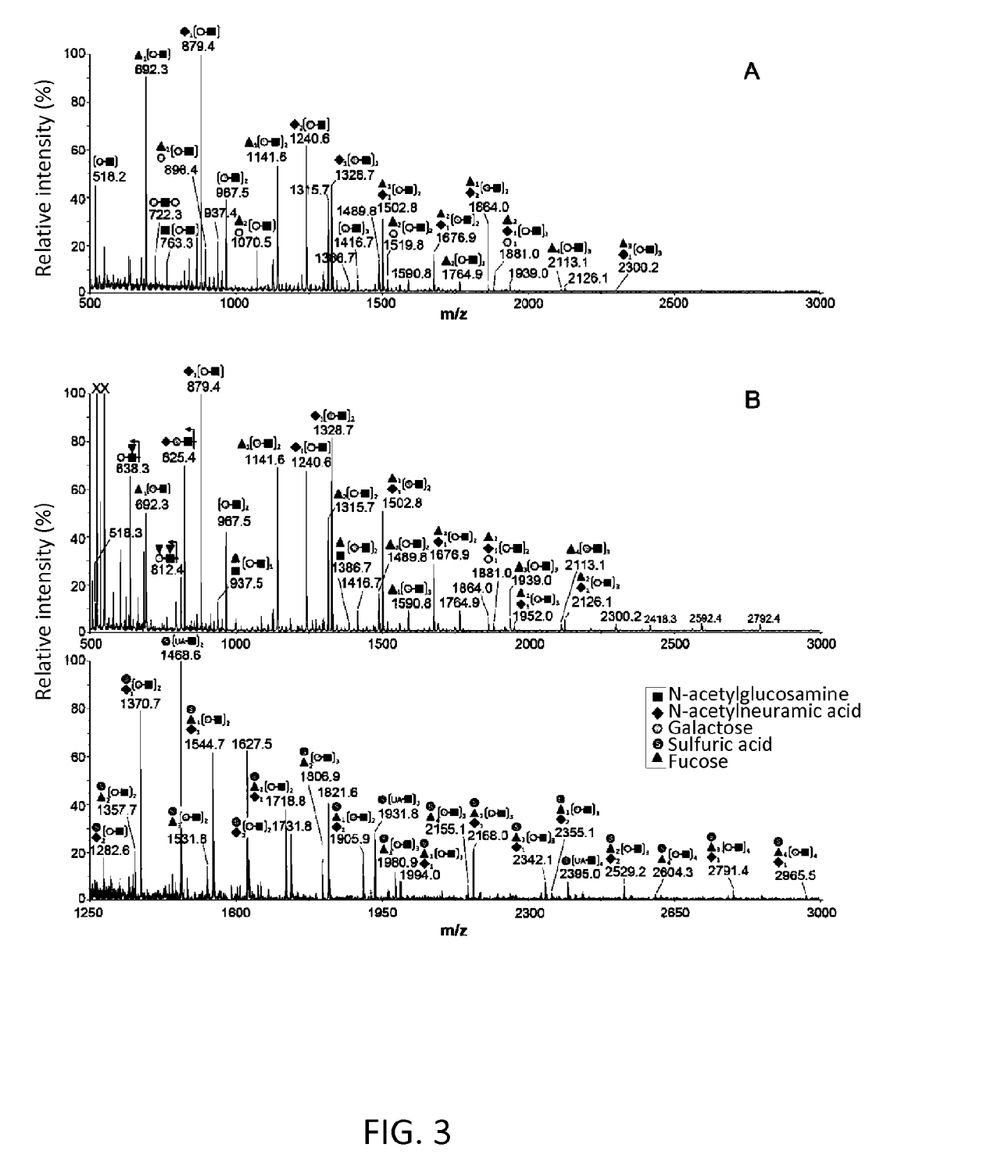
FIG. 3 shows the MALDI-MS spectrums of sperm-associated mucin glycans.
Figure 7:
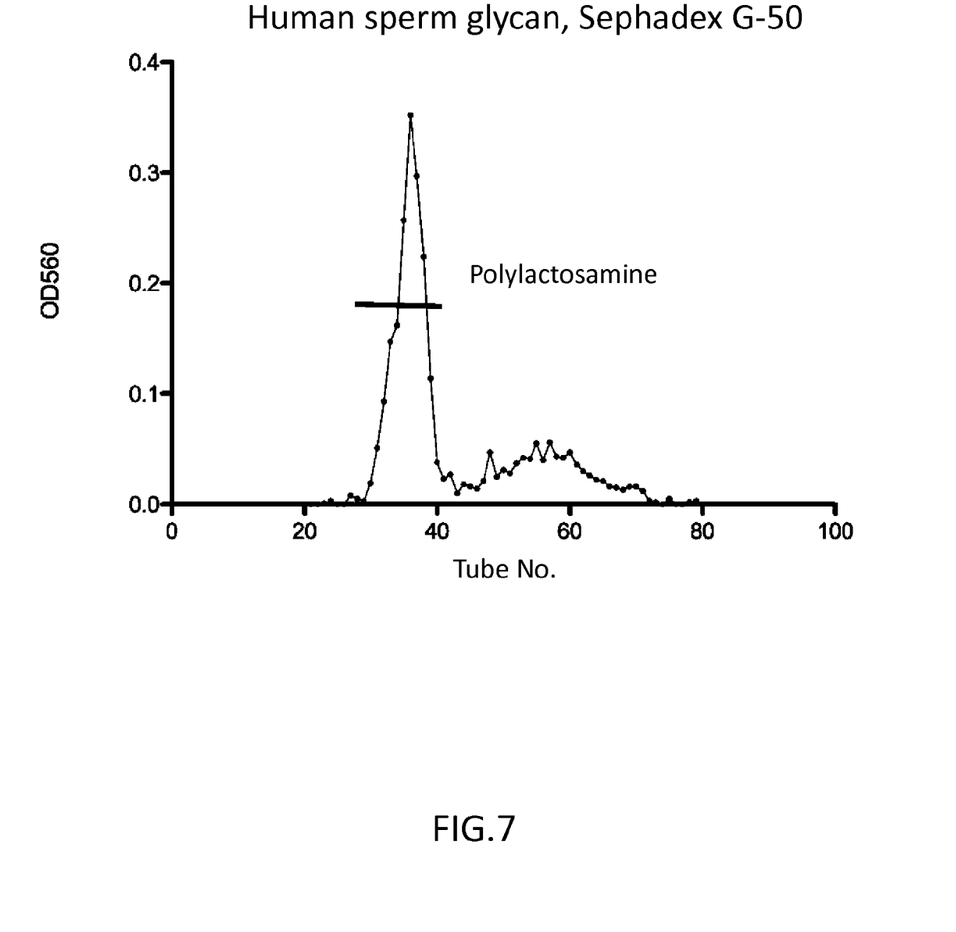
FIG. 7 shows the results of gel filtration chromatography of a human sperm glycopeptide by Sephadex G-50. Each fraction was measured for hexose by an Anthrone color reaction.

As a result of the analysis, it was demonstrated that a sugar chain having a large molecular weight, conceivably a polylactosamine, is present (FIG. 7). The fragment was treated with endo-β-galactosidase and subjected to MALDI-MS. As a result, a series of fragments of 0-2 Fuc LacNAc-Gal glycan were detected. These represent terminal sequences released by the enzyme digestion and have a highly fucosylated 1-3 Hex-HexNAc unit (FIG. 3A). These are probably derived from a polylactosamine terminal highly resistant to the digestion treatment. More complete profile of the non-reducing terminal sequence was previously obtained by MALDI-MS of a sample not treated with endo-β-galactosidase and directly subjected to complete methylation. Owing to this analysis, extremely similar profiles (except that LacNAc-Gal series released by the enzyme treatment were not present) were given in a positive ion mode (FIG. 3B). In addition, it was found that a Hex-HexNAc unit sulfated, sialylated and fucosylated is further present in a negative ion mode (FIG. 3C). In particular, it was clearly found, from both structural analysis and additional MS/MS spectrometry, that H, LeX and LeY epitopes were present (not shown in Figure). Particularly, oxonium ions are generated at m/z 638 and 812 by in-source fragmentation. This result corresponds to LacNAc having Fuc at 1 and 2. In addition, a polysaccharide (glycan) fragment having structures of LacNAc at 3 and Fuc at 4 was detected by the presence or absence of a sulfate. Accordingly, a sperm-associated polylactosamine is not only sialylated and sulfated, but also highly substituted with Fuc containing H, LeX and LeY antigens of a blood group.

FIG. 3 shows MALDI-MS spectra of sperm-associated mucin glycan. Reference panel A shows completely methylated glycan fragments provided by an endo-β-galactosidase treatment of a sample in a positive ion mode and correspond to i) terminal $Fuc_{0-2}$LacNAc-Gal (m/z 722, 896 and 1070) and ii) $[Hex-HexNAc]_{1-3}$ series fucocylated and sialylated at various levels or not. The latter series are not derived from endo-β-galactosidase digestion but may be possibly derived from direct chemical cleavage of a large glycopeptide and/or resistant polylactosamine during complete methylation. Reference panel B shows non-sulfated glycan fragments (upper panel) and sulfated glycan fragments (lower panel) which were provided by complete methylation of the same sample not digested with endo-β-galactosidase, and which were detected in a positive ion mode and a negative ion mode (respectively represented by $[M+Na]^+$ and $[M-H]^-$). In addition to the same series of $[Hex-HexNAc]_{1-3}$ glycan fragments variously fucosylated, terminal H/LeX (m/z 638), LeY (m/z 812) and sialyl LacNAc (m/z 825) were detected. Sulfated and fucosylated $[Hex-HexNAc]_{1-4}$ fragment sialylated or not in a negative ion mode can be identified together with a series of signals. This can be temporality determined to belong to sulfated $[hexuronic acid-HexNAc]_{2-4}$, which is analogous to a repeat unit of glycosamino glycan. All main peaks are labeled with reference symbols as shown in the figure and commented. UA represents hexuronic acid.

Figure 4:
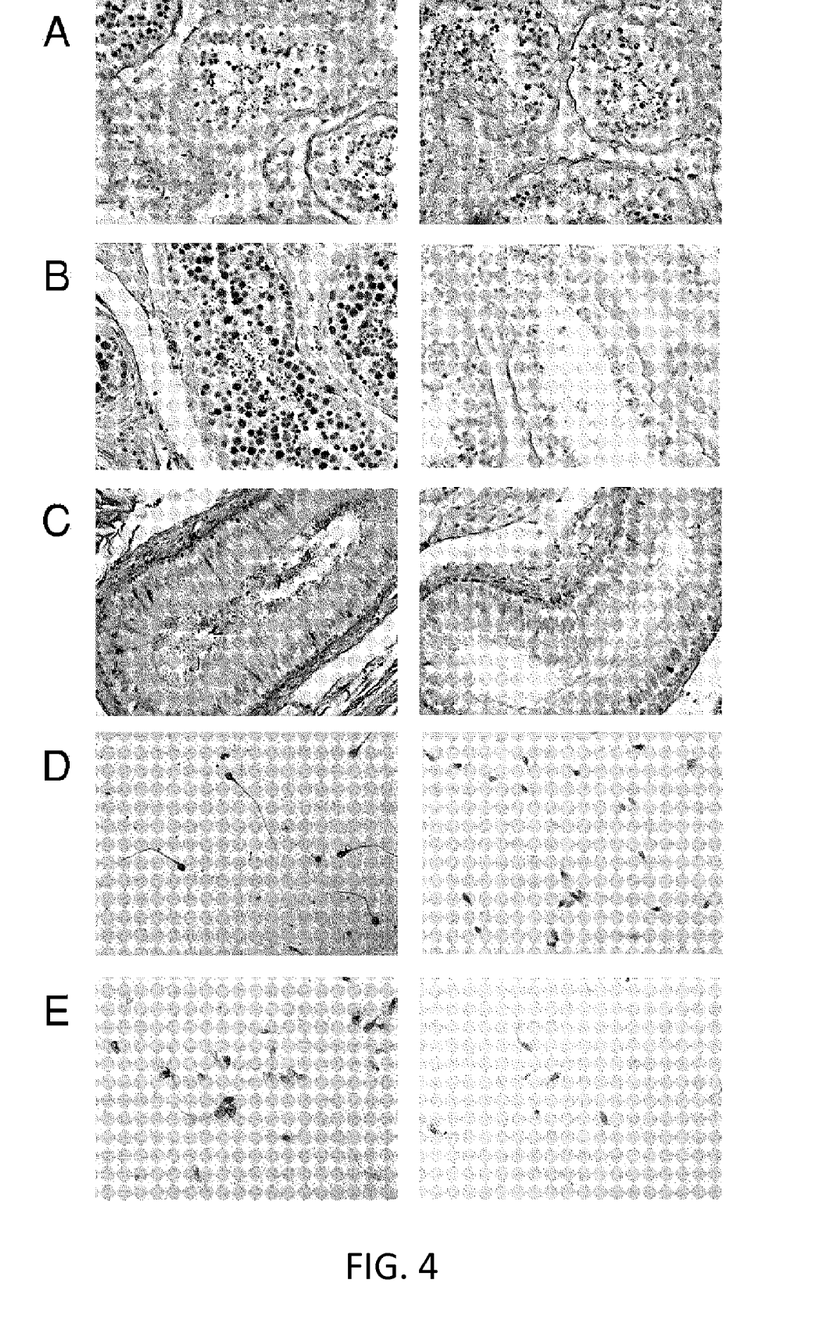
FIG. 4 shows immunohistochemical staining of tissue slices and seminal-fluid smears with an anti-Lewis Y antibody. Reference symbol A shows the testis; B ductuli epididymics; C ductuli efferentes testis; D human seminal fluid; and E sperm washed with PBS. Slides of a tissue slice and the seminal fluid or sperm smear were treated with endo-β-galactosidase (right) or not (left) and immunostained with an anti-Lewis Y antibody. Note that the spermatogonial cells (pointed by an arrow in A) in the testis were not stained; however, the epithelial cells (pointed by a short arrow in B) of the ductuli epididymics and the mucosal fluid (pointed by a long arrow in C) of the ductuli efferentes testis were positively stained by the antibody. Scale bar: 100 μm (A, B and C) and 50 μm (D and E).

(3) Localization of Endo-β-Galactosidase Sensitive LeY Antigen in Organ Functioning in Spermatogenesis To specify an origin of a polylactosamine (found as a sperm associated glycan) of LeY antigen, the present inventors conducted immunohistochemical studies on human tissues derived from organs functioning in spermatogenesis. Human testis was negative against LeY antigen (FIG. 4A). In contrast, LeY antigen was found in the tissue derived from the ductuli epididymics (FIG. 4B) containing newly released sperm cells from the testis and in the epithelial cell of the tissue derived from ductuli efferentes testis (FIG. 4C) containing completely matured sperm cells. The seminal-fluid smear containing a mixture of sperm cells and the seminal fluid was positive to LeY antigen (FIG. 4D). When a LeY positive tissue was treated with endo-β-galactosidase, the tissue was no longer LeY positive (FIGS. 4A to E, right panels). These results strongly suggest that a fucosylated polylactosamine attached to matured sperm cells is derived from the epithelial cells of the epididymis and secreted from the cells to the seminal fluid.

Figure 5:
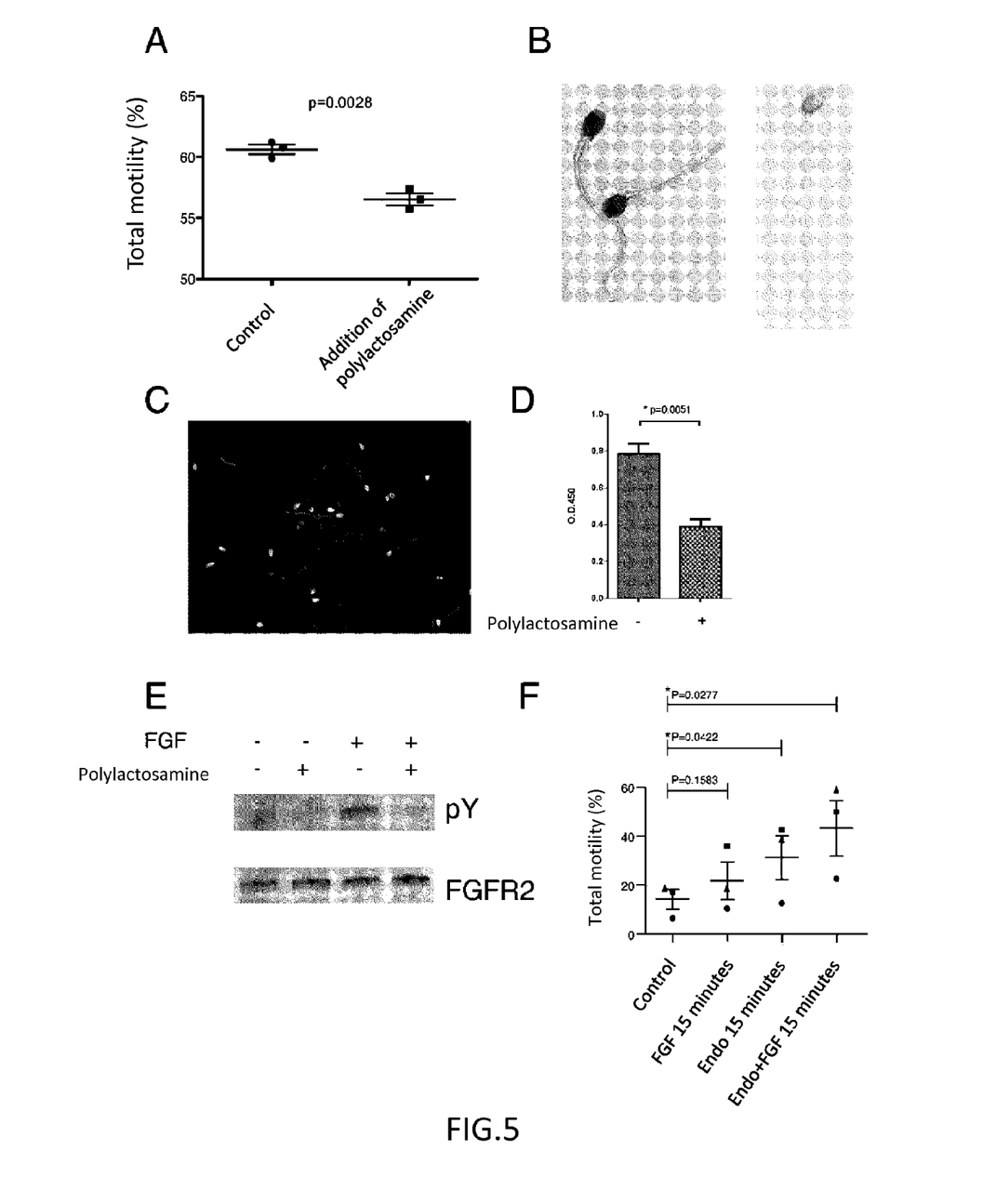
FIG. 5 shows the effects of a polylactosamine derived from the seminal fluid on human sperm cells and HEK293T cells.
Figure 8:
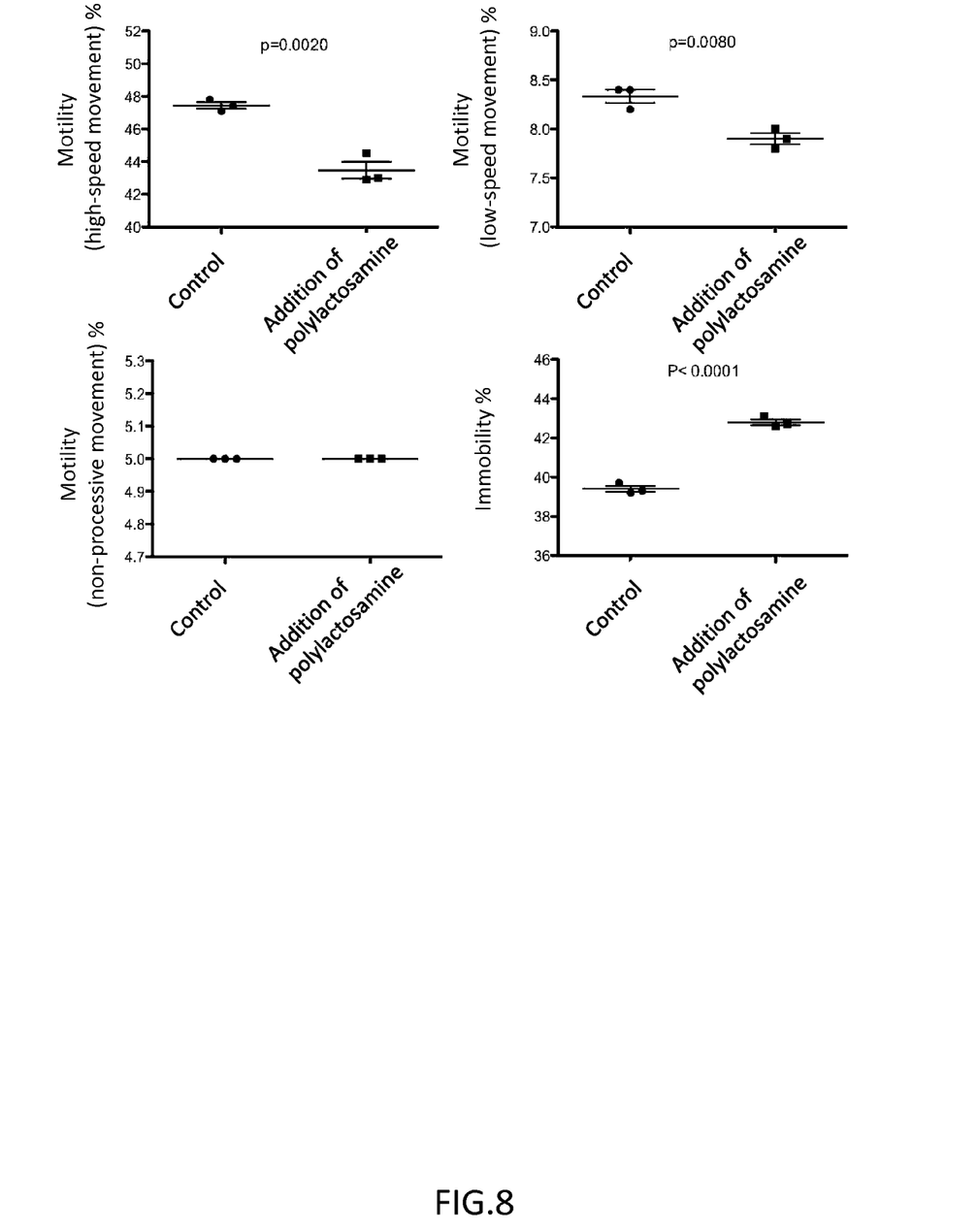
FIG. 8 shows the results of CASA of human sperm in the cases where the spermatic polylactosamine is exogenously added and not added.

(4) Identification of FGFR2 Considered as a Candidate of Polylactosamine Receptor When the spermatic polylactosamine purified from the seminal fluid was added to human sperm cells, sperm motility was suppressed (FIG. 5A, FIG. 8). From this, it is suggested that a polylactosamine receptor of suppressing sperm motility is present in sperm tail. To understand a basic mechanism of a polylactosamine-dependent sperm motility and identify a possible polylactosamine receptor, the present inventors checked proteomics database of human sperm tail proteins (Table 2).

TABLE 2

Table showing part of human sperm tail proteins identified by proteomics

| Score | Name of Protein | Localization |
| --- | --- | --- |
| 1.000 | SPAG4 (sperm associated antigen 4) | Cytoplasm |
| 0.446 | ODF1 (outer defence fiber sperm 1) | Cytoplasm |
| 0.355 | ODF4 (outer defence fiber sperm 4) | Cytoplasm |
| 0.332 | SPAG5 (sperm associated antigen 5) | Cytoplasm |
| 0.278 | CATSPER1 (cation chennel of sperm 1) | Surface of cell |
| 0.276 | ODF3 (Outer defence fiber of sperm 3) | Cytoplasm |
| 0.246 | CCDC65 (coiled coil containing protein 65) | Cytoplasm |
| 0.235 | PPP1CC (protein phosphatase 1) | Cytoplasm |
| 0.230 | FGFR2 (Fibroblast growth factor receptor 2) | Surface of cell |
| 0.218 | APOA1BP (apolipoproteinA1 binding protein) | Secretory |
| 0.215 | AURKC (protein kinase 13) | Cytoplasm |
| 0.215 | RNF38 (ring finger protein 38) | Cytoplasm, Nucleus |
| 0.174 | TAF7L (TAF7 like RNA polymerase) | Nucleus |
| 0.172 | NPHP1 (nephronophthisis) | Cytoplasm |
| 0.158 | PLK1 (polo like kinase 1) | Cytoplasm |
| 0.150 | SPEF2 (sperm flagellar 2) | Cytoplasm |
| 0.150 | SLC26A8 (solute carrier family 26A8) | Surface of cell |
| 0.123 | BSG (beisigin) | Surface of cell |
| 0.121 | SLC16A10 (solute carrier family 16) | Surface of cell |
| 0.120 | SLC25A31 (solute carrier family 25A31) | Surface of cell |
| 0.119 | DNAI2 (dynein, axonemal, intermediate chain 2) | Cytoplasm |
| 0.118 | TSGA10 (testis specific antigen 10) | Nucleus |
| 0.109 | SORD (sorbitol dehydrogenase) | Cytoplasm |
| 0.102 | RSPH1 (radial spoke head 1 homolog) | Nucleus |
| 0.100 | Pcdp1 (primary ciliary dyskinesia protein 1) | Cytoplasm |
| 0.089 | TRIP6 (thyroid hormone receptor interactor 6) | Cytoplasm |

Of several candidates, the present inventors focused attention to FGFR2 by the reason that FGFR2 was observed in the surface of sperm tail (FIG. 5B), and that FGFR2 was reported to increase the cAMP level through the PLCγ/$Ca^{2+}$/PKC pathway.

Figure 9:
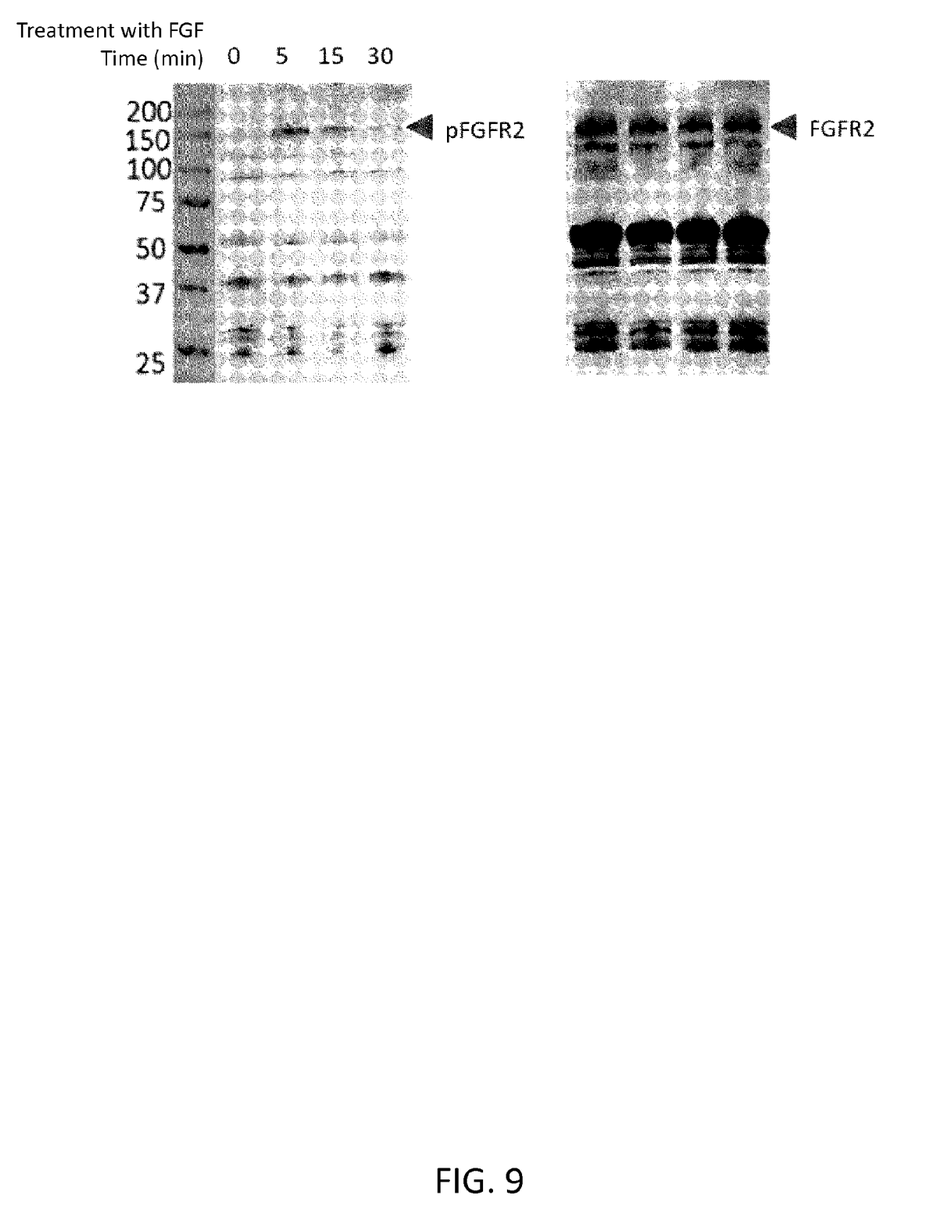
FIG. 9 shows the results of an experiment in which time-dependent change of tyrosine phosphorylation of FGFR2 in the HEK293T cells treated with FGF was checked.

FGFR2 is a receptor tyrosine kinase. When FGF binds to an extracellular domain of FGFR2, tyrosine residues in the cytoplasmic domain of FGFR2 are phosphorylated. When human sperm cells are stained with anti-tyrosine phosphorylation antibody, not the head but the tail was intensively stained (FIG. 5C). Since the intensity and frequency of the staining did not change in the presence or absence of FGF and a polylactosamine (data are not shown), it is suggested that the effects of a polylactosamine and FGF are not easily determined by use of human sperm cells. Thus, the present inventors used HEK293T cells expressing endogenic FGFR2. When FGF was added to the culture solution of HEK293T cells, tyrosine residues in FGFR2 was phosphorylated and the phosphorylation reached a peak in 5 minutes (FIG. 9). When binding of FGF to HEK293T cells in the presence of a polylactosamine was further assayed, the degree of binding was lower than in the absence of a polylactosamine (FIG. 5D). This suggests that a polylactosamine blocks binding of FGF to a receptor. The present inventors finally observed that FGF-dependent tyrosine phosphorylation of FGFR2 in HEK293T cells was inhibited by a polylactosamine (FIG. 5E). Finally, when motility of human sperm cells treated with endo-β-galactosidase and/or FGF was compared, the highest motility was observed in the sperm cells treated with endo-β-galactosidase and FGF (FIG. 5F). These results suggest that FGFR2 activation can be inhibited by blocking binding of FGF to the receptor by the spermatic polylactosamine.

FIG. 5 shows the effect of a polylactosamine derived from the seminal fluid on human sperm cells and HEK293T cells. Reference panel A shows the effect of the spermatic polylactosamine on human sperm motility analyzed by CASA. Motility is represented by the relative number of motile sperm cells relative to the total number of sperm cells used in the analysis. Additional data are shown in FIG. 8. Reference panel B shows immuno-stained human sperm cells, FGFR2 of the cells being stained, wherein the left view shows typical images of human sperm cells stained with an anti-FGFR2 antibody; whereas the right view shows a typical image of a human sperm cell stained without using a primary antibody. Reference panel C shows an immunofluorescent micrograph of stained human sperm cells for tyrosine phosphorylation. The human sperm cells were stained with anti-tyrosine phosphorylation antibody and subsequently with Alexa 564-bound anti-mouse IgG antibody. Diamidino-2-phenylindole was used for staining nuclei. Reference panel D shows the effect of a polylactosamine on binding of FGF to HEK293T cells. The binding in the presence or absence of a polylactosamine was analyzed by FGF-ELISA inhibition assay. Reference panel E shows the effect of a polylactosamine on tyrosine phosphorylation of FGFR2 in HEK293T cells. HEK293T cells were treated with FGF in the presence or absence of a polylactosamine and immunoprecipitation of a lysate was performed by use of an antibody against FGFR2 and immunoblot for phosphorylated tyrosine was performed (lower panel). Reference panel F shows the effect of FGF on motility of human sperm cells treated with endo-β-galactosidase.

Figure 6:
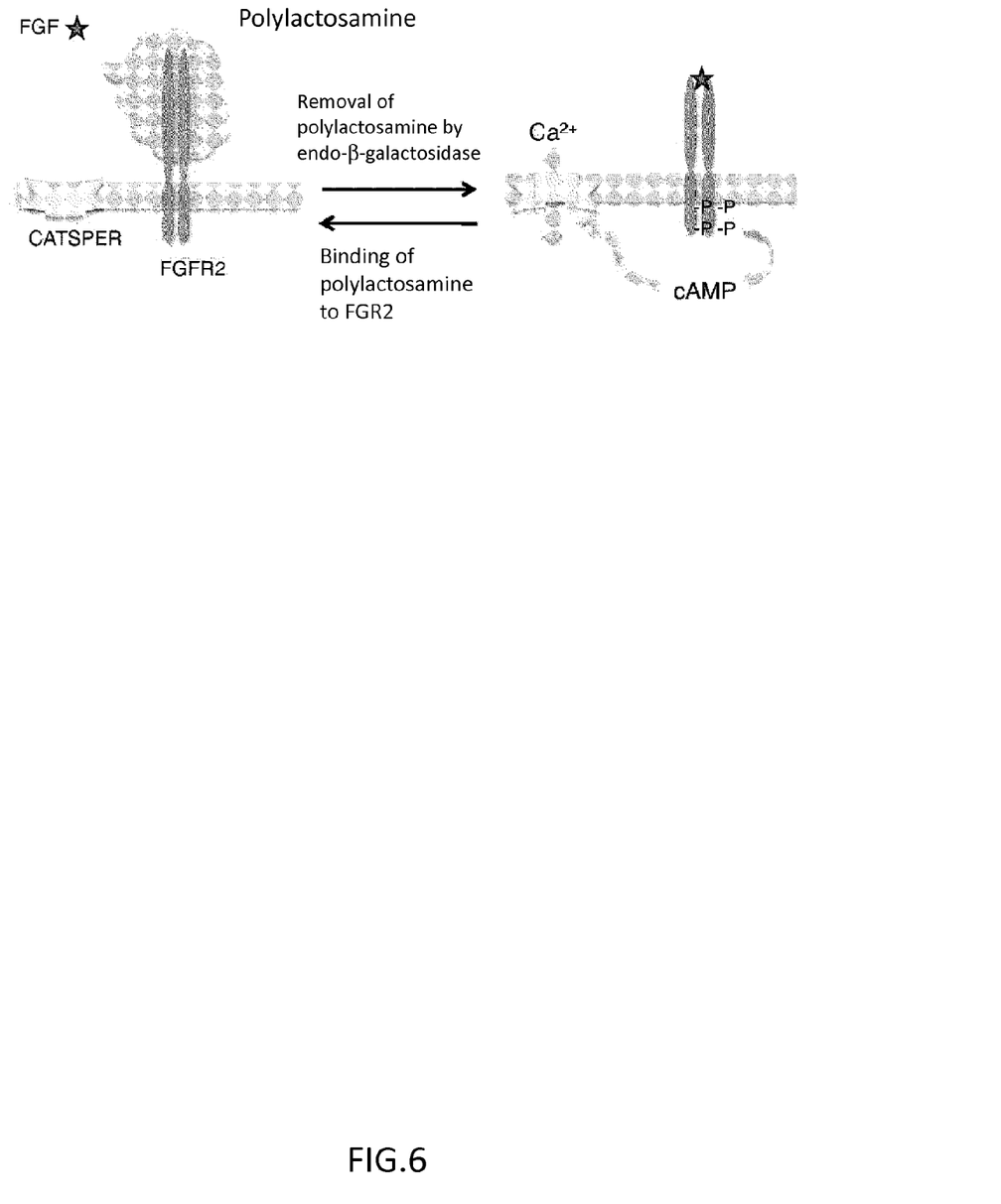
FIG. 6 illustrates an estimated mechanism as to a polylactosamine-dependent suppression of sperm motility.

FIG. 6 illustrates an estimated mechanism as to a polylactosamine dependent suppression of sperm motility. Sperm tail expresses FGFR2 (receptor tyrosine kinase) and CATSPER1 (cAMP dependent calcium channel) and can be associated through a pathway using cAMP. When a spermatic polylactosamine (polyLac) binds to an FGFR2 extracellular domain, binding of FGF to a receptor is inhibited and possibly suppresses sperm motility (left). When the polylactosamine is digested and eliminated with endo-β-galactosidase, FGF can immediately bind to FGFR2 and tyrosine residues of the receptor may be phosphorylated. Subsequently, FGFR2 activation causes signal transduction of PLCγ and PKC and may enhance the influx of calcium accelerating sperm motility, by the cyclic nucleotide sensitivity channel (right).

FIG. 9 shows experimental results of a time-dependent change of tyrosine phosphorylation of FGFR2 in the HEK293T cells treated with FGF. The cells treated with 25 ng/mL of FGF for the time indicated in the figure were subjected to immunoprecipitation with an anti-FGFR2 antibody and subsequently subjected to immunoblot with an anti-tyrosine phosphorylation (10E4) antibody (left). After the antibody was removed, the filter was replobed with the anti-FGFR2 antibody.

INDUSTRIAL APPLICABILITY

Owing to the present invention, it is possible to provide a sperm activating agent and a sperm activating method based on a completely new action mechanism. The activating agent and activating method of the present invention can be utilized in-vitro fertilization and embryo transplantation (IVF-ET) of mammals including humans. In addition, it is considered that the present invention can tremendously improve the efficiency of artificial insemination by husband (AIH) for patients with infertility caused by sperm immotility.

The invention claimed is:

1. A method of activating a sperm comprising:
 (a) incubating the sperm in the presence of endo-β-galactosidase and FGF for up to 60 minutes to activate the sperm; or
 (b) incubating the sperm, which has been endo-β-galactosidase treated, in the presence of FGF for up to 60 minutes to activate the sperm.

2. The method according to claim 1, wherein the FGF is bFGF.

3. The method according to claim 1, wherein the sperm is incubated for up to 30 minutes.

4. The method according to claim 1, wherein the sperm is incubated for up to 15 minutes.

5. The method according to claim 1, wherein the sperm is incubated for about 5 minutes, about 15 minutes, or about 30 minutes.

6. The method according to claim 1, wherein the sperm is incubated at about 37° C.

7. The method according to claim 1, wherein the sperm is incubated under 1% to 15% $CO_2$ atmospheres.

8. The method according to claim 1, wherein the sperm is incubated under 5% $CO_2$ atmospheres.

* * * * *